United States Patent [19]
Arpe et al.

[11] 4,041,039
[45] Aug. 9, 1977

[54] PROCESS FOR PREPARING 2-ETHYL-PYRIDINE

[75] Inventors: Hans-Jürgen Arpe, Fischbach, Taunus; Hansjörg Hey, Langenhain, Taunus, both of Germany

[73] Assignee: Hoechst Aktiengesellschaft, Frankfurt am Main, Germany

[21] Appl. No.: 658,571

[22] Filed: Feb. 17, 1976

Related U.S. Application Data

[62] Division of Ser. No. 476,992, June 6, 1974, Pat. No. 3,957,792.

[30] Foreign Application Priority Data

June 8, 1973   Germany .............................. 2329389

[51] Int. Cl.$^2$ ......................................... C07D 213/06

[52] U.S. Cl. ........................... 260/290 R; 252/455 R; 252/456; 252/462

[58] Field of Search ..................................... 260/290 R

[56] References Cited

U.S. PATENT DOCUMENTS

3,957,792    5/1976    Arpe et al. ...................... 260/290 R

*Primary Examiner*—Alan L. Rotman
*Attorney, Agent, or Firm*—Curtis, Morris & Safford

[57] ABSTRACT

Process for the manufacture of 2-ethyl-pyridine from 2-methyl-pyridine and methanol in the gaseous phase with a catalyst consisting essentially of silicon dioxide and oxides of metals of the second and/or third main group or subgroup and/or the fifth main group of the periodic system of elements at elevated temperatures.

16 Claims, No Drawings

PROCESS FOR PREPARING 2-ETHYL-PYRIDINE

This application is a divisional of copending application Ser. No. 476,992, filed June 6, 1974, which issued on May 18, 1976 as U.S. Pat. No. 3,957,792.

The present invention is a catalytic process for methylation of 2-methyl-pyridine (α-picoline) with methanol to yield 2-ethyl-pyridine.

It is known to those skilled in the art that 2-ethyl-pyridine can be prepared from 2-methyl-pyridine by reacting the latter with methyl-halide in the presence of sodium amide (Bull. soc. chim. France 3, 1607 (1936)). However, this laboratory method is not applicable to technological processes on an industrial scale, due to the unsatisfactory yield rate and the costly reagents.

Furthermore, methylation at the methyl group of α-picoline can be carried out in the gaseous phase starting with aqueous formaldehyde solutions according to U.S. Pat. No. 2,786,846 (1953). The by-product, α-vinyl-pyridine, shows the reaction to develop via a 2-hydroxy-ethyl-pyridine which converts to vinyl-pyridine while separating water. Therefore, formation of 2-ethyl-pyridine from vinyl-pyridine requires an additional hydrogenation step, the hydrogen needs of which have to be satisfied by the initial materials — for example — by decomposition to formaldehyde. This is the reason why this methylation — in respect to the formaldehyde — can yield but a poor result. The examples given in U.S. Pat. No. 2,786,846 do not include any quantitative specifications about the yield or the selectivities of 2-ethyl-pyridine.

The process described by Japanese Patent no. 4.637.592 (1971) also provides for methylation of α-picoline with formaldehyde in the gaseous phase. The highest selectivity of ethyl-pyridine, 57%, is obtained at 510° C by means of a $BPO_4$. $SiO_2$ catalyst. Actually, the selectivity indicated there is related only to the conversion rate of α-picoline, and no statement is given about the selectivity in respect to formaldehyde.

In case of preparation of 2-ethyl-pyridine from 2-methyl-pyridine according to British Patent no. 906 469 (1960) a mixture of an aqueous formaldehyde solution and methanol in the presence of a condensation catalyst is used, the best conversion rate obtainable from 2-methyl-pyridine into 2-ethyl-pyridine and 2-vinyl-pyridine is a maximum 8.3 mol%.

Therefore, as compared to the above mentioned processes which use formaldehyde, a process for preparing 2-ethyl-pyridine from 2-methyl-pyridine exclusively with methanol and under elimination of water represents a very economical form of alkylation.

Another known process reacts methanol with 2-methyl-pyridine at 350° C and under pressure of 200–210 atmospheres in the presence of hydrogen chloride. No statements are given about yield or selectivity; there is merely confirmed that 2-ethyl-pyridines, 2-isopropyl-pyridines and pyridines alkylated in the nucleus are formed. Upon application of this method the use of hydrochloric acid may cause corrosion. Furthermore, the selectivity of 2ethyl-pyridine is unsatisfactory due to the formation of by-products.

The present invention now relates to a process for preparing 2-ethyl-pyridine from 2-methyl-pyridine and methanol wherein the reaction is carried out in the gaseous phase with a catalyst consisting essentially of silicon dioxide and oxides of metals belonging to the second and/or third main- or subgroup and/or to the fifth main group of the periodic system of elements at temperatures from 200° – 600° C, preferably from 300° – 500° C.

Upon comparison to all the processes hitherto known the process according to the present invention offers the great advantage that methanol is used in an economical methylation. Besides, a simple normal-pressure reaction of special catalysts being set up in fixed positions and usually not prone to corrosion, preferably of didymium oxide ($Di_2O_3$) catalysts, achieves economically interesting selectivities of 2-ethyl-pyridine.

When reacting at the catalyst according to the invention, the proportion of methanol to 2-methyl-pyridine can vary within wide limits, for example, covering a range from 1:1 up to 20:1.

Since water is a reaction product of the methylation, the reaction components are not necessarily required to be dry.

Methanol may also contain a certain amount of dimethyl-ether since the reaction according to the invention performed with an acid catalyst may allow for a cleavage of the ether with the reaction water to yield methanol.

The catalyst according to the invention is a mixture of $SiO_2$ — in the form of kieselguhr or silica gel — with oxides of the metals belonging to the second and/or third main group or subgroup and/or to the fifth main group of the periodic system of elements, such as — for example — oxides of magnesium, zinc, cadmium, aluminium, lanthanum, antimony, bismuth or with oxides of rare earths. Rare earths (lanthanides) are the elements having the periodic numbers 58 to 71, i.e. from cerium to lutetium inclusive.

The oxides of rare earths can be used either individually, such as — for example — cerium oxide, but also as mixtures, for example as the commercial didymium oxides $Di_2O_3$ having a composition of lanthanum, cerium, praseodymium, neodymium and small amounts of samarium, gadolinium, ytterbium and others.

The mixture of $SiO_2$ with oxides of the above metals may be prepared according to known methods, for example the simultaneous precipitation of $SiO_2$ and oxides or hydroxides of said metals from water/soluble salts, for example by raising the pH; or the impregnation of $SiO_2$ in the form of kieselguhr or silicagel having a suitable pore structure with aqueous solutions of inorganic salts, for example chlorides, nitrates or organic salts, for example acetates; conversion to oxides or oxide hydrates by alkaline treatment, thermolysis, oxidation or reduction. In order to obtain a catalyst as active and selective as possible for the composition according to this invention, it is advantageous to calcine the catalyst in a determined temperature range after the cited metal salts have been converted to the oxides or oxide hydrates.

The calcination of the oxide mixture may be carried out by heating to temperatures of from 150° to 850° C, preferably from 300° to 600° C. The calcination time is not critical, may vary from 1 to 30 hours and advantageously is from 3 to 15 hours. After this pretreatment, the oxides may partially be present independently of each other, but they may have also reacted, either to give structures similar to silicates, or completely to form silicates having acidic properties.

Therefore, commercial silicates display also a certain catalytic activity for the reaction according to this invention.

Thus, for example, aluminum silicate in its usual form as cracking catalyst or as decationized zeolithe (molecular sieve) may be used for the methylation of 2-methyl-pyridine.

In a similar manner as in the case of the combination of $SiO_2$ and several metal oxides, it is possible to prepare mixed silicates, starting from decationized molecular sieves, by exchange of protons for the ions of the metals which may be used in accordance with this invention, and to employ them advantageously.

The amount of metal oxide relative to $SiO_2$ may widely vary. Advantageous is a concentration of from 0.2 to 25 weight % but higher concentrations may also be used.

The methylation according to the process of the invention is carried out at temperatures of from 200° to 600° C, preferably from 300° to 500° C. A vaporous mixture of the reactants methanol and 2-methyl-pyridine, optionally with addition of an inert diluent such as nitrogen or argon, are passed over the catalyst in the gaseous phase. The catalyst is arranged either in a fixed bed, or, in the case of the gaseous phase, it is fluidized by means of the vaporized starting products to form a fluidized bed. The residence time is from 0.1 to 100 seconds, preferably from 1 to 30 seconds.

The reaction is generally carried out under normal pressure, but it is also possible to operate under lower or elevated pressure.

After condensation of the reaction products, the components are separated and the methylated amines are obtained in known manner, for example by distillation or extraction distillation. Non-reacted starting products may be fed back into the reaction.

The 2-ethyl-pyridine is an important intermediate product also for preparing 2-vinyl-pyridine being used for synthetic rubber, fibers, adhesives and coatings. Furthermore, 2-ethyl-pyridine is an intermediate for pharmaceutical products, for example tuberculostatics.

The following examples illustrate the invention; they were carried out in the following manner:

The catalyst according to the invention placed inside a glass reactor (320 mm length, 21 mm diameter) is heated to a constant temperature by two electric ovens, the temperature being measured inside the reactor by means of a sliding thermoelement. The upper third of the glass reactor is used as evaporator and the two lower thirds function as reacting tube. The reaction products are collected in two cooling traps which are cooled with dry ice/butanol to abt. −70° C.

After a preparatory period of generally two hours for adjusting constant operational conditions, the catalyst test as such is performed over a longer period.

By means of an exterior standard, the reaction products and the non-converted starting products in the united condensates are analyzed by gas chromatography. Generally, the reaction mixture is then separated by distillation.

The values cited in the examples respecting conversion rate, selectivity and yield are defined as follows:

The conversion rate of 2-methyl-pyridine is the molar fraction in percent of the 2-methyl-pyridine converted, calculated on the 2-methyl-pyridine used.

The selectivity of 2-ethyl-pyridine is its molar quantity in percent, calculated on the converted 2-methyl-pyridne.

The 2-ethyl-pyridine yield is the molar quantity in percent, calculated on the 2-methyl-pyridine used.

EXAMPLES 1 – 6

100 ml of $SiO_2$ (pore volume 0.8 ml of $H_2O/g$, surface 160 – 180 m²/g, diameter 0.5 – 1.5 mm) are impregnated with the quantities specified in the following table of metal oxides (applied in the form of aqueous solutions of the corresponding acetates or nitrates) dried and, while passing through 8–10 l of hydrogen, heated to 170° C for two hours and finally to 300° C for another two hours.

Over each of these catalysts 9 ml/per hour of a 2:1 molar mixture of methanol and 2-methyl-pyridine are reacted under normal pressure and at temperatures from 430–470° C, the results obtained are the following conversion rates of 2-methyl-pyridine (MP) as well as the selectivities of 2-ethyl-pyridine (EP).

| Example No. | Metal oxide | mMol | conversion, Mol-% MP | selectivity, Mol-% EP |
|---|---|---|---|---|
| 1 | MgO | 12,5 | 52 | 58 |
| 2 | BaO | 12,5 | 18 | 70 |
| 3 | $Di_2O_3$ | 12,5 | 28 | 89 |
| 4 | $Ce_2O_3$ | 12,5 | 29 | 78 |
| 5 | $Bi_2O_3$ + $Di_2O_3$ | 4,0+25 | 34 | 91 |
| 6 | $Sb_2O_3$ | 25 | 31 | 86 |

EXAMPLE 7

100 ml of $SiO_2$ (pore volume 0.65 ml of $H_2O/g$, surface 120 120 m²/g, diameter 0.5 – 1.5 mm) are impregnated with a solution of 5.25 g of $Di_2O_3$ in 35 ml of glacial acetic acid, pre-dried on a steam bath and subsequently vacuum dried at 140° C in a rotation evaporator. Finally, the catalyst is calcined for 3 hours at 400° C.

13,5 ml per hour of a 4:1 molar mixture of methanol and 2-methyl-pyridine are passed over this catalyst at 480° C and under normal pressure. At a conversion rate of 47 mol % of 2-methyl-pyridine, a selectivity of 2-ethyl-pyridine of 93 mol % is achieved.

In case that the impregnated catalyst is calcined at 500° C for 15 hours after having been dried, under the otherwise identical conditions the conversion rate of 2-methyl-pyridine increases to 53 mol % at almost the same selectivity of 2-ethyl-pyridine.

The test being run for several hours, fractional distillation is carried out with an efficient column. After separation of the unreacted starting materials methanol and 2-methyl-pyridine, 2-ethyl-pyridine (boiling point: 148°–149° C) can be obtained in a yield of 46 mol %.

What is claimed is:

1. A process for the preparation of 2-ethyl-pyridine which comprises reacting 2-methyl-pyridine and methanol in the gaseous state at a reaction temperature in the range of about 200° C to about 600° C. in the presence of a catalyst composition consisting essentially of silicon dioxide and (a) an oxide of bismuth, (b) oxides of bismuth and antimony, (c) oxides of bismuth, antimony and an element of the lanthanide series of the Periodic System or a mixture thereof, or (d) oxides of antimony and an element of the lanthanide series of the Periodic System or a mixture thereof, to form 2-ethyl-pyridine, which catalyst composition is activated by heating to about 150° C. to about 850° C.

2. A process according to claim 1 wherein said catalyst composition contains about 0.2% to about 25% by weight of said oxides (a) through (d) based on the weight of said silicon dioxide.

3. A process according to claim 1 wherein said reaction temperature is in the range of about 300° C. to about 500° C.

4. A process according to claim 1 wherein said methanol and said 2-methyl-pyridine are in proportion of about 1:1 to about 20:1 by weight.

5. A process according to claim 1 wherein said silicon dioxide of said catalyst composition is in the form of kieselguhr or silica gel.

6. A process according to claim 1 wherein the mixture of elements of the lanthanide series contains lanthanum, cerium, praseodymium, neodymium, samarium, gadolinium or ytterbium.

7. The process of claim 1 wherein the catalyst consists essentially of silicon dioxide and an oxide of bismuth.

8. The process of claim 1 wherein the catalyst consists essentially of silicon dioxide and oxides of bismuth and antimony.

9. The process of claim 1 wherein the catalyst consists essentially of silicon dioxide and oxides of bismuth, antimony and an element of the lanthanide series of the Periodic System or a mixture thereof.

10. The process of claim 1 wherein the catalyst consists essentially of silicon dioxide and oxides of antimony and an element of the lanthanide series of the Periodic System or a mixture thereof.

11. A process for the preparation of 2-ethyl-pyridine which comprises reacting 2-methyl-pyridine and methanol in the gaseous state at a reaction temperature in the range of about 200° C to about 600° C in the presence of a catalyst composition consisting essentially of silicon dioxide and an oxide of antimony to form 2-ethyl-pyridine, which catalyst composition is activated by heating to about 150° C to about 850° C.

12. A process according to claim 11 wherein said catalyst composition contains about 0.2% to about 25% by weight of said antimony oxide based on the weight of said silicon dioxide.

13. A process according to claim 11 wherein said reaction temperature is in the range of about 300° C to about 500° C.

14. A process for the preparation of 2-ethyl-pyridine which comprises reacting 2-methyl-pyridine and methanol in the gaseous state at a reaction temperature in the range of about 200° C to about 600° C in the presence of a catalyst composition consisting essentially of silicon dioxide, an oxide of bismuth and an element of the lanthanide series of the Periodic System or a mixture thereof to form 2-ethyl-pyridine, which catalyst composition is activated by heating to about 150° C to about 850° C.

15. A process according to claim 14 wherein said catalyst composition contains about 0.2% to about 25% by weight of said oxide and element of the lanthanide series based on the weight of said silicon dioxide.

16. A process according to claim 14 wherein said reaction temperature is in the range of about 300° C to about 500° C.

* * * * *